US011337758B2

(12) United States Patent
Deibel et al.

(10) Patent No.: US 11,337,758 B2
(45) Date of Patent: May 24, 2022

(54) CONDITIONING A LASER-TISSUE CONTACT SURFACE

(71) Applicant: ADVANCED OSTEOTOMY TOOLS—AOT AG, Basel (CH)

(72) Inventors: Waldemar Deibel, Wrexen/Diemelstadt (DE); Thomas Richter, Münster (DE); Alfredo E. Bruno, Biel-Benken (CH)

(73) Assignee: ADVANCED OSTEOTOMY TOOLS—AOT AG, Basel (CH)

( * ) Notice: Subject to any disclaimer, the term of this patent is extended or adjusted under 35 U.S.C. 154(b) by 635 days.

(21) Appl. No.: 15/748,405

(22) PCT Filed: Jul. 27, 2016

(86) PCT No.: PCT/EP2016/067957
§ 371 (c)(1),
(2) Date: Jan. 29, 2018

(87) PCT Pub. No.: WO2017/025335
PCT Pub. Date: Feb. 16, 2017

(65) Prior Publication Data
US 2018/0214207 A1 Aug. 2, 2018

(30) Foreign Application Priority Data
Aug. 7, 2015 (EP) .................................. 15180233

(51) Int. Cl.
*A61B 18/20* (2006.01)
*A61B 90/00* (2016.01)
(Continued)

(52) U.S. Cl.
CPC .......... *A61B 18/20* (2013.01); *A61B 17/3203* (2013.01); *A61B 90/05* (2016.02);
(Continued)

(58) Field of Classification Search
CPC .................... A61B 18/20; A61B 18/26; A61B 2018/00005; A61B 2018/00029;
(Continued)

(56) References Cited

U.S. PATENT DOCUMENTS

| 4,069,823 A * | 1/1978 | Isakov ................... A61B 18/20 606/11 |
| 5,865,182 A * | 2/1999 | Chen ...................... A61B 90/50 128/846 |
| 6,544,256 B1 * | 4/2003 | Rizoiu ................... A61B 18/26 604/20 |
| 2002/0045811 A1 * | 4/2002 | Kittrell .............. A61B 1/00096 600/407 |

(Continued)

OTHER PUBLICATIONS

International Search Report for International Application No. PCT/EP2016/067957 dated Oct. 31, 2016 (4 Sheets).
(Continued)

*Primary Examiner* — Nathan R Price
*Assistant Examiner* — Justin L Zamory
(74) *Attorney, Agent, or Firm* — Kratz, Quintos & Hanson, LLP (57) ABSTRACT

A nozzle device (1) comprises a plurality of multi-fluid nozzles (5) and a body (2) with a bore (8). The bore (8) has a laser entrance (82) and a laser exit (81). The nozzle device (1) is adapted to be mounted to a laser medical device such that a laser beam generated by the laser medical device enters the laser entrance (82) of the bore (8) of the body (2) and exits the laser exit (81) of the bore (8) of the body (2). The body (2) houses the multi-fluid nozzles (5) and the multi-fluid nozzles (5) are arranged around the laser exit (81) of the bore (8) of the body (2). The nozzle device (1) allows to conditioning a tissue at and near where it is cut or drilled by the laser beam of the laser medical device. Thus, the nozzle device (1) is particularly suitable for a laser
(Continued)

osteotomic device allowing to minimize collateral damages of the tissue when being cut or drilled.

20 Claims, 4 Drawing Sheets

(51) Int. Cl.
    *A61B 17/3203*    (2006.01)
    *A61B 18/00*    (2006.01)

(52) U.S. Cl.
    CPC ........ *A61B 2018/00005* (2013.01); *A61B 2018/00029* (2013.01); *A61B 2018/00565* (2013.01); *A61B 2018/00601* (2013.01); *A61B 2090/049* (2016.02); *A61B 2090/0418* (2016.02); *A61B 2218/003* (2013.01); *A61B 2218/007* (2013.01)

(58) Field of Classification Search
    CPC ......... A61B 2018/00565; A61B 2018/00601; A61B 2218/003; A61B 2218/007
    See application file for complete search history.

(56) References Cited

U.S. PATENT DOCUMENTS

| | | | |
|---|---|---|---|
| 2002/0120260 A1* | 8/2002 | Morris | A61B 18/1477 606/41 |
| 2005/0212879 A1* | 9/2005 | Chiao | B05B 5/1691 347/86 |
| 2005/0256517 A1* | 11/2005 | Boutoussov | A61B 17/3203 606/16 |
| 2009/0143773 A1* | 6/2009 | Gosse | A61B 18/203 606/12 |
| 2012/0172874 A1* | 7/2012 | Fischer | H05H 1/46 606/49 |
| 2014/0257254 A1 | 9/2014 | Boutoussov | |

OTHER PUBLICATIONS

Written Opinion of the International Searching Authority for International Application No. PCT/EP2016/067957 dated Oct. 31, 2016 (5 Sheets).

\* cited by examiner

CONDITIONING A LASER-TISSUE CONTACT SURFACE

TECHNICAL FIELD

The present invention relates to a nozzle device for a laser medical device and a respective nozzle device set. Such devices and sets can be used for conditioning a laser-tissue contact surface in a process of treating the tissue by means of a laser beam delivered by the laser medical device. In particular such treating can relate to cutting a bone or a similar human or animal hard tissue.

BACKGROUND ART

For cutting and drilling materials in various technical fields it has become increasingly popular to use apparatuses which apply a laser beam to the material. Today, in industrial applications such laser cutting or drilling is widespread since it allows for efficiently and flexibly process work pieces at high precision. Also, for cutting human or animal hard or soft tissue such like bones, cartilages or the like laser cutting and drilling with laser is more and more applied. For example, in computer assisted surgery it is known to use a laser beam as cutting instrument. More particularly, e.g., in WO 2011/035792 A1 a computer assisted and robot guided laser osteotomic medical device is described which allows for precise and gentle drilling and cutting of bone and other human or animal hard and also soft tissue.

Within such laser drilling and cutting particularly in the medical field conditioning the material or tissue in an area where it is hit by the laser beam can be of importance. For example, to guarantee an efficient and clean controlled execution of robot-guided laser cuts in hard and soft tissue it is crucial to achieve as few dehydration of the tissue around the drill or cut from the ablation as possible. Also, dissipation of the heat from the cut into the tissue structure can have disadvantageous effects such as melting which are aimed to be prevented as far as possible.

In this context, there is a need for a device or system allowing to condition the tissue or material at and near where the tissue is treated by a laser beam in order to minimize collateral damages of the tissue and material. In particular, there is a need for such a device or system which can be used in laser osteotomic devices.

DISCLOSURE OF THE INVENTION

According to the invention this need is settled by a nozzle device as it is defined by the features of independent claim 1 and by a nozzle device set as it is defined by independent claim 20. Preferred embodiments are subject of the dependent claims.

The gist of the invention is the following: A nozzle device for conditioning a laser-tissue contact area comprises a plurality of multi-fluid nozzles and a body with a bore. The bore has a laser entrance and a laser exit. Thereby, the nozzle device is adapted to be mounted to a laser medical device such that a laser beam generated by the laser medical device enters the laser entrance of the bore of the body and exits the laser exit of the bore of the body. The body houses the multi-fluid nozzles and the multi-fluid nozzles are arranged around the laser exit of the bore of the body.

The term "tissue" in the context of the invention can relate to hard or soft human or animal tissue. Particularly, it can relate to bone tissue, finger or toe nail tissue, cartilage tissue or the like.

The laser medical device can particularly be a laser osteotome. By the laser beam entering the laser entrance of the bore and exiting the laser exit of the bore the laser beam passes the bore of the body. The bore can particularly be a straight bore. Thus, the laser beam can straightly pass the bore and the body.

The term "laser-tissue contact area" as used herein relates to an area of the tissue at and around which it is hit by the laser beam when the laser medical device is operated. For being mountable to the laser medical device in order that a laser beam generated by the laser medical device can pass the bore, the body can be connected to the laser medical device with the laser entrance of the bore facing towards the laser medical device and the laser exit of the bore projecting away from the laser medical device. Therefore, the laser medical device can have a mounting structure securing the nozzle device at the laser medical device in a precise predefined position.

The multi-fluid nozzles can particularly be two-fluid nozzles. They typically can be spray nozzles facilitating dispersion of a liquid such as water or a 0.9% NaCI-solution and a gas such as air into a spray. Like this, the nozzles can efficiently moisturize and cool the laser-tissue contact area. Generally, spray nozzles can be categorized based on the energy input used to breakup of the liquid into drops. They can have one or more outlets wherein a multiple outlet nozzle can be referred to as a compound nozzle.

By providing the nozzle device with a plurality of multi-fluid nozzles around its laser exit it can efficiently condition the laser-tissue contact area. In this context the term "conditioning" can particularly comprise moisturizing and cooling the tissue at the laser-tissue contact area. The plurality of nozzles is advantageously uniformly distributed around the laser exit and adjusted to be focused on the laser-tissue contact area. Advantageously, they are positioned and oriented such that the sprays generated are focused at or near the laser-tissue contact area.

The nozzle device according to the invention allows for an intervention such as a cut or a drill to the tissue with minimum or no carbonization around the area of intervention. Dehydration of the tissue around the intervention can be minimized or eliminated by moisturizing the ablation zone and the surrounding tissue. Furthermore, the nozzle device can prevent heat to dissipate further away from the intervention area through the cooling effect introduced by the kinetic energy of the nozzles' sprays or vapor and the absorption of excessive energy through the cooling liquid itself. Like this, the nozzle device allows to conditioning the tissue at and near where it is cut or drilled by the laser beam of the laser medical device. Thus, the nozzle device is particularly suitable for a laser osteotomic device and allows to minimize collateral damages of the tissue.

Preferably, the multi-fluid nozzles have a spray direction which is adjustable. In this connection the term "spray direction" can relate to a main or central direction a spray is ejected from the respective multi-fluid nozzle. It is understood that multi-fluid nozzles generally generate a spray with droplets travelling in varying directions over a certain angle. Nevertheless such a spray has a main orientation being the spray direction.

By having a flexibly adjustable spray direction the sprays of all of the multi-fluid nozzles can be focused on the laser-tissue contact area in variable environments. For example, the tissues can be placed at different places in front of the nozzle device and the nozzles can be adjusted to the respective distance between the tissue and the nozzle device. This allows for using the same nozzle device types for different work distances. Or, the focus of the sprays of the nozzles can be adjusted with increasing ablation of the tissue. This can particularly be beneficial when comparably deep drills or cuts are applied.

For adjusting the spray direction of the nozzles the nozzle device can have a control unit. Such control unit allows for precisely adjusting the nozzles. Also, an automated adjustment is possible.

Preferably, the plurality of multi-fluid nozzles comprises three, four, five or six multi-fluid nozzles regularly arranged around the laser exit of the bore of the body. When the bore of the body has a circular cross section the multi-fluid nozzles can be 120°, 90°, 72° or 60° offset to each other depending on the number of nozzles included. Such a number of multi-fluid nozzles allows for evenly and efficiently conditioning the laser-tissue contact area.

The multi-fluid nozzles can generate a spray by distributing or atomizing the liquid which can be caused by the interaction of high velocity gas and liquid. Thereby, compressed air can conveniently be used as the atomizing gas but steam or other gases are also possible. The multi-fluid nozzles can be internal mix nozzles in which the fluids, typically a gas and a liquid, contact inside the nozzle. Shearing between high velocity gas and low velocity liquid can disintegrate the liquid stream into droplets producing a comparably high velocity spray.

However, preferably the multi-fluid nozzles are external-mix multi-fluid nozzles. Typically, in external-mix nozzles fluids contact outside the nozzle itself. This type of spray nozzle may require more atomizing air and a higher atomizing air pressure drop because the mixing and atomization of liquid takes place outside the nozzle. The liquid pressure drop can be lower for this type of nozzles, sometimes drawing liquid into the nozzle due to the suction caused by the atomizing air nozzles. This spray may be shaped to efficiently produce a variety of different spray patterns. For example, a flat pattern can be formed with additional air to flatten or reshape the circular spray cross-section discharge. Such external-mix nozzles allow for a comparably precise and flexible adjustment of the provided spray.

The multi-fluid nozzles of the nozzle device according to the invention are built for a precise regulation of the volume flows of gas and liquid. A fluid increase at constant pressure enlarges the droplets of the resulting vapor or spray and hence produces a bigger moisturizing effect. Bigger droplets could also be used to enhance the purge qualities of the vapour or spray. A constant spray with a higher pressure produces finer droplets. This results in a bigger cooling effect through the increased kinetic energy stored in the finer droplets. Such a spray also enables a better uncontested penetration in thinner cuts or drills, thus preventing a water film and ensuring a constant tissue cooling.

Preferably, the body comprises a plurality of stacked plates. Such plates can be rings or ring-like shaped. They can be manufactures of any suitably material such as a robust plastic or metal. Different plates can be made of different materials. A body formed of stacked plates allows for a flexible assembling of the nozzle device. Also it allows for efficiently providing a nozzle device adapted to a specific application, i.e. a convenient customization of the nozzle device or system. Further, the stacked plates embodiments of the nozzle device allow for easily integrate a variety of functions into the system.

Thereby, the plurality of stacked plates preferably comprises a gas supply plate. This gas supply plate has a gas chamber for each of the multi-fluid nozzles, a gas supply channel for each of the gas chambers, and a through bore being part of the bore of the body. Thereby, the through bore of the gas supply plate comprises the laser exit of the bore of the body, each of the gas supply channels is connected to one of the gas chambers, and each of the gas chambers has an outlet being the outlet of the respective multi-fluid nozzle. As mentioned above the gas can particularly be air. Such gas supply plate allows for easily and efficiently integrate the function of supplying a gas into the multi-fluid nozzles. Such gas supply can be required for producing and tuning the sprays of the nozzles.

Also, the plurality of stacked plates preferably comprises a liquid supply plate. This liquid supply plate has a liquid chamber or homogenizer chamber for each of the multi-fluid nozzles, a liquid supply channel for each of the liquid chambers, a liquid emission channel, and a through bore being part of the bore of the body. Each of the liquid supply channels is connected to one of the liquid chambers, each of the liquid chambers is connected to one of the liquid emission channels, and each of the liquid emission channels extends through one of the gas chambers of the gas supply plate to the outlet of said one of the gas chambers of the gas supply plate. Like this, the function of supplying liquid to the multi-fluid nozzles can efficiently be integrated. Also, by the liquid emission channels extending through the gas chambers external mix multi-fluid nozzles can efficiently be provided in the nozzle device. The liquid emission channels can also be single part set into the liquid chambers.

In some interventions it is crucial to be able to bring the vaporization or spraying into a pulsing mode or to stop it completely, e.g., to clean the operation area or to reposition the laser head of the laser medical device. In this context, each of the multi-fluid nozzles preferably comprises a gas supply equipped with a valve. The valves can be fluently or stepwise controllable or they can be simple on/off valves. All of the gas supplies of the multi-fluid nozzles together can have one single valve such that all multi-fluid nozzles are equipped with the same single gas supply valve. Alternatively, each of the multi-fluid valves can be equipped with its own valve such that the number of gas supply valves is identical to the number of multi-fluid nozzles. It is also possible that some of the multi-fluid nozzles are equipped with a single valve such that groups of multi-fluid nozzles are built by single gas supply valves. Also, individual gas supply valves can be combined with one central gas supply valve such that the gas supply can be adjusted in the individual multi-fluid nozzles as well as the gas supply can centrally be controlled such as stopped.

In embodiments of the nozzle device including a gas supply plate the gas supplies can be formed by the gas supply channels. By means of one or plural gas supply valves an efficient adjustment of the gas stream in the multi-fluid nozzles can be achieved. For example, by closing a gas supply valve the spray of the associated multi-fluid nozzle(s) can rapidly be stopped which can be beneficial in various applications. The gas supply valves can be precisely adjusted by a control unit.

The gas supply valves advantageously are fast pressure regulation valves which allow to achieve necessary opening times, e.g. 0.2 seconds, to be able to pulse the vapour or spray. For example, the spray can be pulsed between drill or cut depth measurements and the cutting process. These methods presume that the initial gas supply stays intact without any pressure loss at all times.

Preferably, each of the multi-fluid nozzles comprises a liquid supply equipped with a valve. Similar as described herein before in connection with the gas supplies all of the liquid supplies of the multi-fluid nozzles together can have one single valve such that all multi-fluid nozzles are equipped with the same single liquid supply valve. Alternatively, each of the multi-fluid valves can be equipped with its own valve such that the number of liquid supply valves is identical to the number of multi-fluid nozzles. Such individual liquid supply valves allow for using different solutions in one set up or intervention. For example, this allows for varying the ratio between a cooling solution and another solution which can be enriched with drugs for wound cleaning.

It is also possible that some of the multi-fluid nozzles are equipped with a single valve such that groups of multi-fluid nozzles are built by single liquid supply valves. In embodiments of the nozzle device including a liquid supply plate the liquid supplies can be formed by the liquid supply channels. By means of one or plural liquid supply valves an efficient adjustment of the liquid stream in the multi-fluid nozzles can be achieved. The liquid supply valves can be precisely adjusted by a control unit which can be a central control unit.

By being able to open and close the multi-fluid nozzle liquid supply at will and to any extent the spray or vapor of the nozzle device can be regulated through variable valve timing. In some embodiments, each single multi-fluid nozzle can individually be stopped if needed. This can, e.g., be beneficial when several solutions are used in the several multi-fluid nozzles. Or, it also allows for only providing gas if needed at a specific stage of the ablation or cutting process. The valves also allow for a comparably fast opening and closing. Like this, a fluid pulsing mode can be provided where the fluid supply is repeatedly turned on and off in a given frequency which, e.g., can be beneficial to dry the cut or drill between laser intervention and a depth control measurement.

In particular, the nozzle device preferably comprises a valve control for opening and closing the valves of the gas supply and the valves of the liquid supply independent from each other.

Preferably, the nozzle device comprises a plurality of light sources arranged around the laser exit of the bore of the body. The light sources can particularly comprise light emitting diodes (LED). In many applications, the target tissue must be well illuminated, so that the operator or surgeon can see the operating area. Furthermore, frequently cameras or other monitoring devices are used in the laser head of the laser medical device in order to monitor the intervention in high quality. By providing the light sources in the nozzle device the need for additional illuminating devices which can be cumbersome to place or precisely operate in many applications can be eliminated. Advantageously, the number of light sources of the nozzle device is chosen to achieve an even and sufficient illumination of the tissue intervention area.

Preferably, the body comprises a RFID chip. Thereby, the acronym RFID relates to radio-frequency identification. In many applications the nozzle device can be operated in a sterile zone. The RFID chip can then ensure that each nozzle device is only used for one application or patient. For example, the laser medical device can have a corresponding detector with which it can identify the mounted nozzle device. Furthermore, the RFID chip allows for monitoring the consumption and for tracing each nozzle device. This can particularly be beneficial for supporting the use of nozzle devices and the like.

Preferably, the nozzle device comprises a gas stream inlet/outlet arranged to suck or blow debris induced by the laser beam generated by the laser medical device. The gas can particularly be air. Such gas stream inlet/outlet allows for removing debris generated by ablation. Particularly, sensitive parts like the optics of the laser medical device, cameras in the laser head, an outcoupling window of the laser medical device or the like can be protected from the debris. Thus, the quality of intervention can be maintained during ablation of the tissue.

Thereby, the plurality of stacked plates preferably comprises a debris protection plate. This debris protection plate has a through bore being part of the bore of the body, an open inner gas chamber directed to the through bore, and a gas stream channel. The through bore of the gas supply plate comprises the laser entrance of the bore of the body and the gas stream channel is connected to the inner gas chamber. In turn, the gas stream channel can be connected to blowing or suction means. Thereby, the debris protection plate preferably comprises an open outer gas chamber oriented to the laser-tissue contact area, wherein a further or the already mentioned gas stream channel is connected to the outer gas chamber. Such a plate within the stacked plates arrangement of the nozzle device allows for an efficient implementation of a debris protection.

Preferably, the nozzle device comprises a base having a through bore, a closure, a laser medical device fixture and a mounting structure. Thereby, the closure is adjustable from a closed position in which it closes the through bore to an open position in which the through bore is open, the laser medical device fixture is arranged to fix the nozzle device to the laser medical device and the mounting structure is arranged to be mounted the body. Such a base allows for conveniently mounting and demounting the body to and from the laser medical device. Also, it is possible that the same base is used for mounting different bodies depending on the needs of the respective application. The closure allows for protecting the laser medical device when the nozzle or its body is demounted. Thereby, the closure preferably is configured such that it is in its closed position when the body is demounted from the base and in its open position when the body is mounted to the base.

Preferably, the nozzle device comprises a window which closes the bore between the laser entrance and the laser exit. Thereby, the window preferably is inclined in relation to an axis of the bore. Like this, a laser beam travelling through the bore does not hit the window in a right angle. Thus, reflection of light into the direction of the laser medical device can be prevented.

Exemplary technical specifications of a possible nozzle device can be the following: outer diameter of 44 mm; inner diameter (bore diameter) of 20 mm, height 50 mm; orientation of the nozzles adjusted for a distance of 75 mm to an operating field and centered on a focal spot of the laser medical device; fluid volume flow from 3 ml per min to 30 ml per min; spray angle of the multi-fluid nozzles of 20° to 25° and a tolerable gas pressure of 0.5 bar to 3.5 bar.

Another aspect of the invention relates to a nozzle device set comprising a nozzle device as described above and a drape. The drape sterilely covers the nozzle device. Thereby, such covering can be a complete or partial covering of the nozzle device. In particular, at least exits of the multi-fluid nozzles though which sprays are ejectable out of the multi-fluid nozzles preferably are outside the drape. Also, other associated devices or parts thereof can be covered by the drape together with the nozzle device. For example, a laser head and/or a robot arm of the laser medical device can be included in the drape together with the nozzle device which, e.g., can be mounted to the laser head.

In many applications the nozzle device can be used within a sterile zone. Thus, either a fixation option for a drape or an integration of the nozzle device in the drape can be beneficial. Benefits of the integration into the drape can be that, since the nozzle device and eventually associated parts can be the last element for the intervention system when being built up, it can be provided in a seal and sterile manner allowing to establish the sterile zone. Furthermore, all supply channels for gas and air can be integrated within the drape, saving time for installation and fixation for other solutions.

BRIEF DESCRIPTION OF THE DRAWINGS

The nozzle device and nozzle device set according to the invention are described in more detail herein below by way of an exemplary embodiment and with reference to the attached drawings, in which.

DESCRIPTION OF EMBODIMENTS

In the following description certain terms are used for reasons of convenience and are not intended to limit the invention. The terms "right", "left", "up", "down", "under" and "above" refer to directions in the figures. The terminology comprises the explicitly mentioned terms as well as their derivations and terms with a similar meaning. Also, spatially relative terms, such as "beneath", "below", "lower", "above", "upper", "proximal", "distal", and the like, may be used to describe one element's or feature's relationship to another element or feature as illustrated in the figures. These spatially relative terms are intended to encompass different positions and orientations of the nozzle device in use or operation in addition to the position and orientation shown in the figures. For example, if the device or a specific part thereof in the figures is turned over, elements described as "below" or "beneath" other elements or features would then be "above" or "over" the other elements or features. Thus, the exemplary term "below" can encompass both positions and orientations of above and below. The device may be otherwise oriented (rotated 90 degrees or at other orientations), and the spatially relative descriptors used herein interpreted accordingly. Likewise, descriptions of movement along and around various axes includes various special device positions and orientations.

To avoid repetition in the figures and the descriptions of the various aspects and illustrative embodiments, it should be understood that many features are common to many aspects and embodiments. Omission of an aspect from a description or figure does not imply that the aspect is missing from embodiments that incorporate that aspect. Instead, the aspect may have been omitted for clarity and to avoid prolix description.

In this context, the following applies to the rest of this description: If, in order to clarify the drawings, a figure contains reference signs which are not explained in the directly associated part of the description, then it is referred to previous or following description sections. Further, for reason of lucidity, if in a drawing not all features of a part are provided with reference signs it is referred to other drawings showing the same part. Like numbers in two or more figures represent the same or similar elements.

Figure 1:
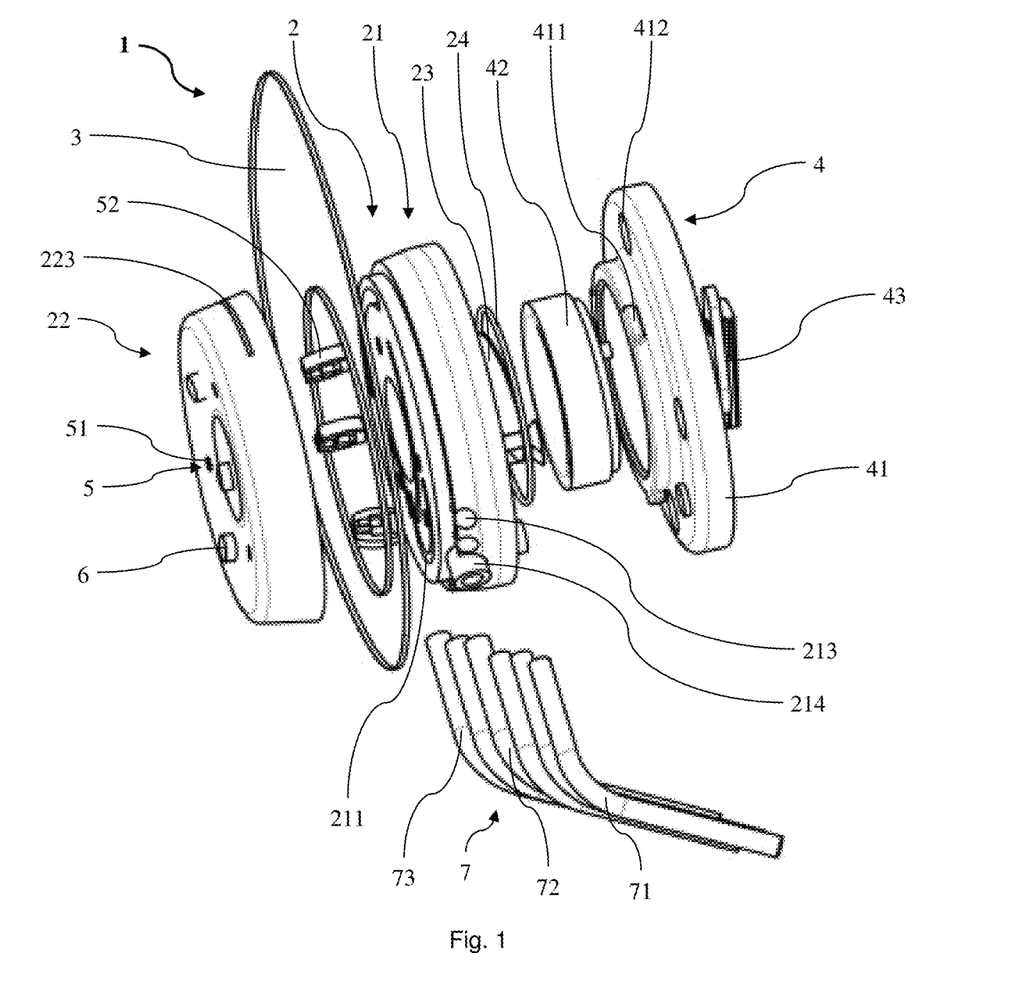
FIG. 1 shows perspective exploded view of an embodiment of a nozzle device according to the invention.

FIG. 1 show an exploded view of an embodiment of a nozzle device 1 according to the invention. The nozzle device 1 comprises a plurality of ring-like shaped and stacked plates as well as other parts which in FIG. 1 are disassembled from each other. In particular, the nozzle device 1 includes a nozzle device base 4 and a body 2. The nozzle device base 4 comprises a flange like base plate 41, a ring shaped diaphragm ring 42 and diaphragm wings 43. The base plate 41 has flat ring section provided with axial screw bores 412 as laser medical device fixture and a rim section. At an outer peripheral surface of the rim section of the base plate 41 male parts 411 of a bayonet fixing are provided as mounting structure.

The body 2 of the nozzle device 1 comprises an essentially ring shaped liquid supply and debris protection plate 21 (in the following referred as LSDP plate 21) neighboring the nozzle device base 4 and an essentially ring shaped gas supply plate 22. At an outer peripheral surface the LSDP plate 21 is equipped with gas ports 213, a power port 214 and liquid ports 215 (not visible in FIG. 1). At a side of the LSDP plate 21 facing the gas supply plate 22 liquid chambers 211 are formed into the LSDP plate 21.

The gas supply plate 22 of the body 2 comprises an inwardly inclined front side of the nozzle device 1 which is equipped with three LEDs 6 as light sources and three openings establishing spray outlets 51 of three two-fluid nozzles 5 as multi-fluid nozzles. Each of the two-fluid nozzles 5 further includes a liquid emission channel 52 and, as showed in more detail below, one of the liquid chambers 211 of the LSDP plate 21. At a peripheral outer surface of the gas supply plate 22 slits 223 are provided being the open end of outer gas chambers 215 arranged in the LSDP plate 21 (not visible in FIG. 1).

Between the nozzle device base 4 and the body 2 an O-ring 24 and a window 23 and between the LSDP plate 21 and the gas supply plate 21 a draping holder 3 are provided. The draping holder 3 basically has an uneven rounded form and is provided with an eccentric round bore. It is made of glass. The nozzle device 1 further comprises a set of media supply lines 7 with gas supply lines 71, a power line 72 and liquid supply lines 73.

Figure 2:
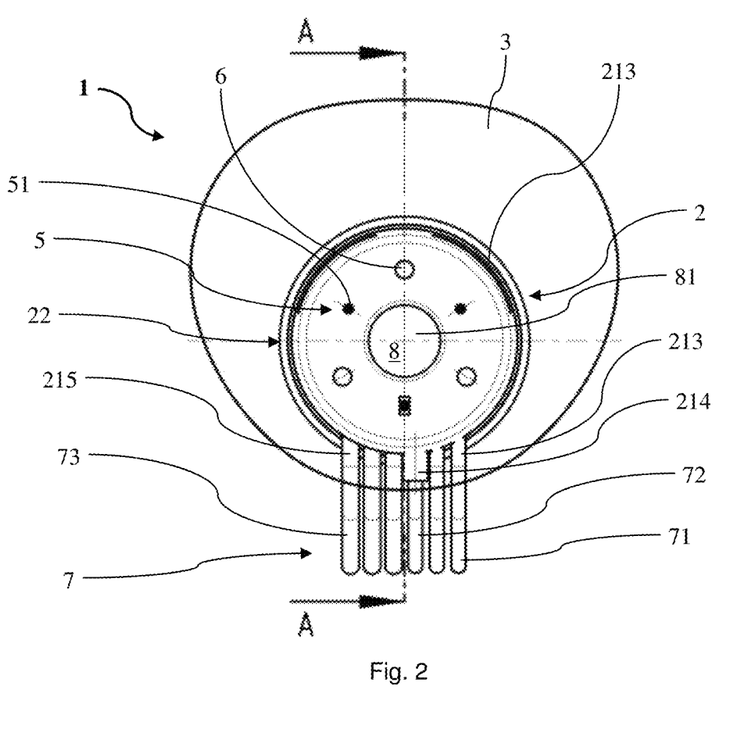
FIG. 2 shows a front view of the nozzle device of FIG. 1.

As can be seen in FIG. 2 in which the nozzle device 1 is shown in an assembled state towards its front end, the gas supply lines 71 are connected to the gas ports 213 of the LSDP plate 21, the power line 72 to its power port 214 and the liquid supply lines 73 to its liquid ports 215. Thereby, the gas ports 213, the power port 214 and the liquid ports 215 lie in one straight line.

The nozzle device 1 has a straight bore 8 extending from its front side at the LSDP plate 22 to the back side at the nozzle device base 4. At the front side of the nozzle device 1 the bore 8 ends in its laser beam exit 81. The spray outlets 51 of the three two-fluid nozzles 5 are regularly arranged around the laser beam exit 81 of the bore 8. Like this, the spray outlets 51 are arranged along a circle in an angle of 120° offset from each other. Centrally between each two neighboring spray outlets 51 one of the LEDs 6 is placed. Thus, also the LEDs 6 are arranged along a circle in an angle of 120° offset from each other.

Figure 3:
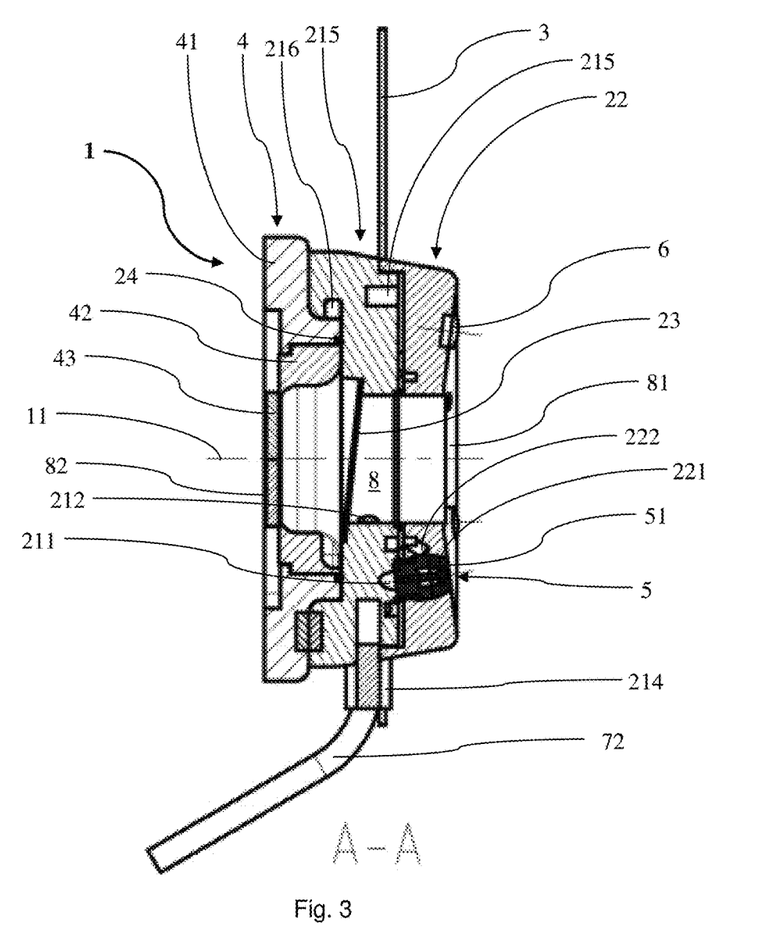
FIG. 3 shows a cross sectional view along the line A-A of FIG. 2.

In FIG. 3 a cross section of the assembled nozzle device 1 is shown. The diaphragm ring 42 is inserted into an opening of the base plate 41. Thereby, the diaphragm ring 42 is turnable inside and relative to the base plate 41. It is further coupled to the diaphragm wings 43 such that turning the diaphragm ring 42 relative to the base plate 41 induces a movement of the diaphragm wings 43. Thereby, the diaphragm wings 43 open and close a laser beam entrance 82 of the bore 8 depending on the turning of the diaphragm ring 42.

At its end side facing the nozzle device base 4, the LSDP plate 22 of the body 2 has a rim recess in which the rim section of the base plate 41 is arranged. More particularly, the rim recess of the LSDP plate 22 has a female portion 216 of the bayonet fixing at a inner ring circumferential surface. By turning the body 2 relative to the nozzle device base 4 around a longitudinal axis of the nozzle device 1 when being arranged on the rim section of the base plate 41 the female portion 216 of the bayonet fixing of the LSDP plate engages the male portion 411 of the bayonet fixing of the base plate 41. Thereby, the body 2 can be locked and unlocked on the nozzle device base 4.

The diaphragm ring 42 is coupled to the LSDP plate 21 when the body 2 is arranged on the nozzle device base 4. Like this, when turning the LSDP plate 21 relative to the base plate 41 the diaphragm ring 42 is also turned relative to the base plate 41. Thereby, the diaphragm wings 43 are opened or closed, respectively. More particularly, when the body 2 is locked on the nozzle device base 4 by turning the LSDP plate 21 relative to the base plate 41 the diaphragm ring 42 is turned to the identical extent and the diaphragm wings 43 are moved apart such that the laser beam entrance 82 of the bore 8 is opened. Vice versa, when the body 2 is unlocked from the nozzle device base 4 by turning the LSDP plate 21 in an opposite direction relative to the base plate 41 the diaphragm ring 42 is turned to the identical extent and the diaphragm wings 43 are moved towards each other such that the laser beam entrance 82 of the bore 8 is closed. In FIG. 2 the body 2 is shown unlocked from the nozzle device base 4 and the laser beam entrance 82 are closed by the diaphragm wings 43 accordingly.

When the body 2 is mounted to the nozzle device base 4 the O-ring 24 is clamped between the LSDP plate 21 and the base plate 41. The O-ring 24 has an elasticity allowing for sealing the connection of the LSDP plate 21 and the base plate 41. Additionally, the O-ring 24 damps movements of the LSDP plate 21 and the base plate 41 relative to each other along a longitudinal axis 11 of the nozzle device 1.

Furthermore, between the LSDP plate 21 and the base plate 41 the window 23 is arranged. Thereby, the window 23 is inclined relative to the longitudinal axis 11 of the nozzle device 1. More specifically, the window 23 and the longitudinal axis 11 lie in an angle of about 84° relative to each other. Like this, it can be prevented that light of a laser beam provided through the bore 8 of the nozzle device 1 is reflected and travelling back to the laser medical device. Rather, laser beam light would be deflected by 12° when being reflected by the window 23 such that it is not sent back to the laser medical device.

As can be seen in FIG. 3 the LSDP plate 21 comprises an inner gas chamber 212 which ends in an opening provided at in inner cylindrical surface of the LSPD plate 21. The inner gas chamber 212 is connected to one of the gas supply lines 71 via one of the gas ports 213 and via a gas stream channel (not visible in FIG. 3). It is further oriented such that gas provided by the respective gas supply line 71 and exiting the opening of the gas chamber 212 hits the window 23. Like this, the window can efficiently be cleaned. In particular, debris generated by ablation can be removed from the window 23 such that provision of the laser beam can be kept at a constant high quality during a ablation process.

The liquid chambers 211 formed in the end side of the LSDP plate 21 facing the gas supply plate 22 are connected to the liquid supply lines 73 via the liquid ports 213 and liquid supply channels (not visible in FIG. 3) such that they can be provided with a liquid to be sprayed by the two-fluid nozzles 5. Each of the liquid supply lines 73 as well as each of the gas supply lines 71 are provided with a valve. The valves can be adjusted and, particularly be switched on and off. By means of the valves, the gas and liquid supply into the two-way nozzles 5 can be controlled.

The gas supply plate 22 comprises gas chambers 221 each being part of one of the two-fluid nozzles 5. The gas chambers 221 connect the spray outlets 51 with the liquid chambers 211. Each of the gas chambers 221 is connected to the gas supply lines 71 via a gas supply channel (not visible in FIG. 3) of the gas supply plate 22 and is provided with one of the liquid emission channels 52. When the two-fluid nozzles are provided with liquid and gas the liquid is pushed via the liquid chambers 211 through the liquid emission channels 52 out of the spray outlet 51. In the meantime the gas is forwarded through the gas chambers 221 out of the spray outlet 51. Outside the two-fluid nozzles 5 the gas stream hits the liquid stream and according sprays are produced. By adjusting the pressure and flow of the gas and the liquid characteristics of the sprays can precisely be defined.

The end side of the gas supply plate 22 has a surface which is inwardly inclined towards the laser beam exit 81. Like this, two-fluid nozzles 5 are directed towards a focal spot. Thus, in a situation where the two-fluid nozzles 5 produce a straight spray the sprays meet in the focal spot. In order that the two-fluid nozzles 5 do not have to be adjusted, the focal spot is preferably located where the laser beam hits the tissue to drill or cut.

Figure 4:
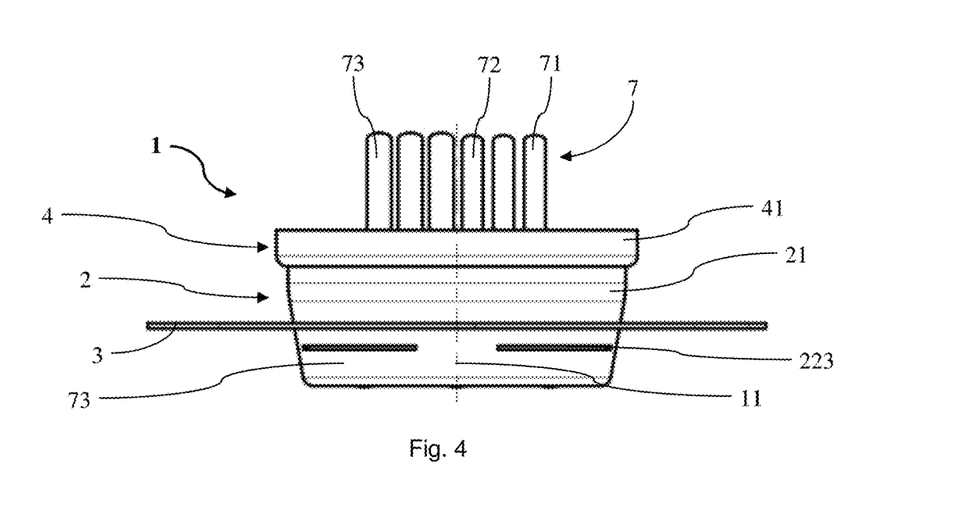
FIG. 4 shows a side view of the nozzle device of FIG. 1.
Figure 5:
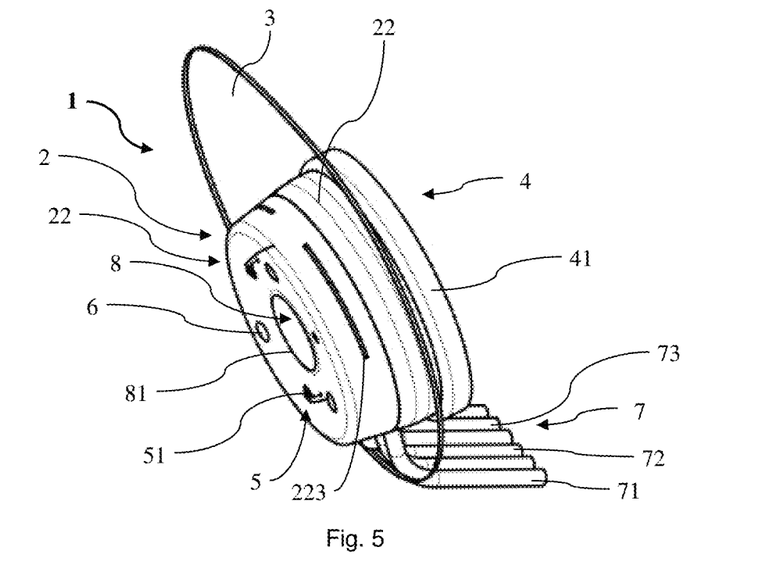
FIG. 5 shows a perspective view of the nozzle device of FIG. 1.

The LSDP plate 21 is further equipped with the outer gas chambers 215 which are connected to the slits 223 in the gas supply plate 22 and to the gas supply lines 71 via the gas ports 213 and a gas stream channel (not visible in FIG. 3). As can be seen in FIG. 4 showing the nozzle device 1 from a side and in FIG. 5 showing the nozzle device in a perspective there are two slits 223 neighboring each other. The outer gas chambers 215 are connected to the gas supply lines 71. By providing gas through the outer gas chambers 215 and out of the slits 223 a gas stream can be produced around a front side of the nozzle device 1. Like this debris produced by ablation can be removed from around the nozzle device 1 and from the laser-tissue contact area.

This description and the accompanying drawings that illustrate aspects and embodiments of the present invention should not be taken as limiting the claims defining the protected invention. In other words, while the invention has been illustrated and described in detail in the drawings and foregoing description, such illustration and description are to be considered illustrative or exemplary and not restrictive. Various mechanical, compositional, structural, electrical, and operational changes may be made without departing from the spirit and scope of this description and the claims. In some instances, well-known circuits, structures and techniques have not been shown in detail in order not to obscure the invention. Thus, it will be understood that changes and modifications may be made by those of ordinary skill within the scope and spirit of the following claims. In particular, the present invention covers further embodiments with any combination of features from different embodiments described above and below.

The disclosure also covers all further features shown in the FIGS. individually although they may not have been described in the afore or following description. Also, single alternatives of the embodiments described in the figures and the description and single alternatives of features thereof can be disclaimed from the subject matter of the invention or from disclosed subject matter. The disclosure comprises subject matter consisting of the features defined in the claims or the exemplary embodiments as well as subject matter comprising said features.

Furthermore, in the claims the word "comprising" does not exclude other elements or steps, and the indefinite article "a" or "an" does not exclude a plurality. A single unit or step may fulfil the functions of several features recited in the claims. The mere fact that certain measures are recited in mutually different dependent claims does not indicate that a combination of these measures cannot be used to advantage. The terms "essentially", "about", "approximately" and the like in connection with an attribute or a value particularly also define exactly the attribute or exactly the value, respectively. The term "about" in the context of a given numerate value or range refers to a value or range that is, e.g., within 20%, within 10%, within 5%, or within 2% of the given value or range. Components described as coupled or connected may be electrically or mechanically directly coupled, or they may be indirectly coupled via one or more intermediate components. Any reference signs in the claims should not be construed as limiting the scope.

The invention claimed is:

1. Nozzle device for conditioning a laser-tissue contact area, comprising a plurality of multi-fluid nozzles, a body with a bore and a base, wherein
   the bore has a laser entrance and a laser exit,
   the nozzle device is adapted to be mounted to a laser medical device such that a laser beam generated by the laser medical device enters the laser entrance of the bore of the body and exits the laser exit of the bore of the body,
   the body houses the multi-fluid nozzles,
   the multi-fluid nozzles are arranged around the laser exit of the bore of the body,
   the base has a through bore, a closure, a laser medical device fixture and a mounting structure,
   the closure of the base is adjustable from a closed position in which it closes the through bore to an open position in which the through bore is open,
   the laser medical device fixture of the base is arranged to fix the nozzle device to the laser medical device, and
   the mounting structure of the base is arranged to mount the body to the base.

2. Nozzle device according to claim 1, wherein the multi-fluid nozzles have a spray direction which is adjustable.

3. Nozzle device according to claim 1, wherein the plurality of multi-fluid nozzles comprises three, four, five or six multi-fluid nozzles regularly arranged around the laser exit of the bore of the body.

4. Nozzle device according to claim 1, wherein the body comprises a plurality of stacked plates.

5. Nozzle device according to claim 4, wherein the plurality of stacked plates comprises a gas supply plate having
   a gas chamber for each of the multi-fluid nozzles,
   a gas supply channel for each of the gas chambers, and
   a through bore being part of the bore of the body, wherein
   the through bore of the gas supply plate comprises the laser exit of the bore of the body,
   each of the gas supply channels is connected to one of the gas chambers, and
   each of the gas chambers has an outlet being the outlet of the respective multi-fluid nozzle.

6. Nozzle device according to claim 5, wherein the plurality of stacked plates comprises a liquid supply plate having
   a liquid chamber for each of the multi-fluid nozzles,
   a liquid supply channel for each of the liquid chambers,
   a liquid emission channel, and
   a through bore being part of the bore of the body, wherein
   each of the liquid supply channels is connected to one of the liquid chambers,
   each of the liquid chambers is connected to one of the liquid emission channels, and
   each of the liquid emission channels extends through one of the gas chambers of the gas supply plate to the outlet of said one of the gas chambers of the gas supply plate.

7. Nozzle device according to claim 1, wherein each of the multi-fluid nozzles comprises a gas supply equipped with a valve.

8. Nozzle device according to claim 1, wherein each of the multi-fluid nozzles comprises a liquid supply equipped with a valve.

9. Nozzle device according to claim 7, comprising a valve control for opening and closing the valves of the gas supply and the valves of the liquid supply independent from each other.

10. Nozzle device according to claim 1, comprising a plurality of light sources arranged around the laser exit of the bore of the body.

11. Nozzle device according to claim 1, wherein the body comprises a RFID chip.

12. Nozzle device according to claim 1, comprising a gas stream inlet/outlet arranged to suck or blow debris induced by the laser beam generated by the laser medical device.

13. Nozzle device according to claim 12, wherein the plurality of stacked plates comprises a debris protection plate having
   a through bore being part of the bore of the body,
   an open inner gas chamber directed to the through bore, and
   a gas stream channel, wherein
   the gas stream channel is connected to the inner gas chamber.

14. Nozzle device according to claim 13, wherein the debris protection plate comprises an open outer gas chamber oriented to the laser-tissue contact area, wherein a gas stream channel is connected to the outer gas chamber.

15. Nozzle device according to claim 1, wherein the closure is configured such that it is in its closed position when the body is demounted from the base and in its open position when the body is mounted to the base.

16. Nozzle device set comprising a nozzle device according to claim 1 and a drape, wherein the drape sterilely covers the nozzle device.

17. Nozzle device according to claim 1, wherein the multi-fluid nozzles are external-mix multi-fluid nozzles.

18. Nozzle device according to claim 1, comprising a window which closes the bore between the laser entrance and the laser exit.

19. Nozzle device according to claim 18, wherein the window is inclined in relation to an axis of the bore.

20. Nozzle device for conditioning a laser-tissue contact area, comprising a plurality of multi-fluid nozzles and a body with a bore, wherein
   the bore has a laser entrance and a laser exit,
   the nozzle device is adapted to be mounted to a laser medical device such that a laser beam generated by the laser medical device enters the laser entrance of the bore of the body and exits the laser exit of the bore of the body,
the body houses the multi-fluid nozzles,
the multi-fluid nozzles are arranged around the laser exit of the bore of the body, and
the body comprises a plurality of stacked plates.

* * * * *